(12) United States Patent
Huttner et al.

(10) Patent No.: US 10,258,543 B1
(45) Date of Patent: Apr. 16, 2019

(54) MEDICAL TUBE UNCLOGGING SYSTEM AND RELATED METHOD

(71) Applicant: Bionix Development Corporation, Toledo, OH (US)

(72) Inventors: James Huttner, Sylvania, OH (US); Josh Noble, Oak Harbor, OH (US); Cody Harder, North Royalton, OH (US)

(73) Assignee: PM Medical Solutions, LLC, Arlington Heights, IL (US)

( * ) Notice: Subject to any disclaimer, the term of this patent is extended or adjusted under 35 U.S.C. 154(b) by 0 days.

(21) Appl. No.: 15/838,574

(22) Filed: Dec. 12, 2017

Related U.S. Application Data

(60) Provisional application No. 62/434,464, filed on Dec. 15, 2016.

(51) Int. Cl.
*A61M 25/00* (2006.01)
*A61J 15/00* (2006.01)
*A61M 1/00* (2006.01)
*A61B 90/70* (2016.01)

(52) U.S. Cl.
CPC ....... *A61J 15/0026* (2013.01); *A61J 15/0011* (2013.01); *A61M 1/0078* (2013.01); *A61B 2090/701* (2016.02); *A61M 2025/0019* (2013.01)

(58) Field of Classification Search
CPC .............. A61J 15/0026; A61J 15/0011; A61M 1/0078; A61M 2025/0019; A61B 2090/701
See application file for complete search history.

(56) References Cited

U.S. PATENT DOCUMENTS

| | | | | |
|---|---|---|---|---|
| 5,290,250 | A * | 3/1994 | Bommarito | A61M 25/04 604/175 |
| 7,611,502 | B2 * | 11/2009 | Daly | A61J 1/1481 215/247 |
| 9,656,022 | B1 * | 5/2017 | Russo | A61M 5/2448 |
| 2011/0098660 | A1 * | 4/2011 | Porreca, Jr. | A61M 25/0026 604/246 |
| 2015/0165496 | A1 | 6/2015 | Moreau | |

OTHER PUBLICATIONS

Halyard Clog Zapper Enteral Device Declogging System, prior to Dec. 15, 2016.
TubeClear Feeding Tube Clearing System, prior to Dec. 15, 2016.
Bionix Enteral Feeding Tube DeCloggers, prior to Dec. 15, 2016.

* cited by examiner

*Primary Examiner* — Sharidan Carrillo
(74) *Attorney, Agent, or Firm* — Marshall & Melhorn, LLC

(57) ABSTRACT

A device is provided for unclogging an enteral tube including a first length of tubing, the distal end of which is fitted with a connector for connecting to an enteral feeding tube and the proximal end of which is fitted with a connector that is not compatible with an enteral feeding tube. An anti-reflux valve is situated in the first length of tubing and allows fluid flow only towards the distal end thereof. A second length of tubing has a proximal end connected to the first length of tubing at a position between the proximal end of the first length of tubing and the directional valve. A pressure relief valve is situated in the second length of tubing. A method is provided for utilizing the device to clear a clogged enteral tube.

17 Claims, 3 Drawing Sheets

MEDICAL TUBE UNCLOGGING SYSTEM AND RELATED METHOD

BACKGROUND OF THE INVENTION

It is a common practice in medicine to use enteral feeding tubes to provide fluids and nutrition to moribund patients. These same enteral tubes may also be used to provide suction allowing emptying and decompression of the stomach and gastrointestinal (GI) tract. Enteral feeding tubes also provide a convenient means to give oral medications to those patients who otherwise could not swallow them; the pills are crushed and administered as a slurry in water through the tube.

Enteral tubes come in a variety of types, French sizes, and lengths depending on the insertion site and intended use. Types include G-tube and J-tubes (relatively short enteral tubes inserted thru surgically created openings in the abdominal wall leading into the gut and usually used for long-term nutrition for debilitated patients), naso-gastric tubes of various types (these may be single or multi-lumen, and can be used for gastric decompression or for administration of enteral nutrition, and generally tend to be long in length), and a variety of specialty enteral tubes placed for nutrition, medications, or other purposes. This latter group tend to be significantly longer tubes with narrow internal diameters and comprised of softer silastic materials; they are often used for extended term enteral feeding and become clogged more easily due to their long length and small bore diameter.

Not infrequently these enteral tubes become obstructed or clogged. This is often the result of the gemisch of nutrient protein solutions, fluid pH levels, administered medications, and pill fragments being incompatible with one another leading to a slug of material that clogs the tube. In these cases, the clog must be dislodged or broken-up so that patency can be restored and the enteral tube can continue to be used. Failure to unclog the enteral tube can necessitate its removal, a costly and time consuming procedure that often requires a trip to the emergency room and the presence of a skilled surgeon or specialist.

Because of the importance of maintaining the patency of enteral feeding tubes, many means have been developed to effect removal or break-up of obstructing clogs. The simplest method is to flush the enteral tube with copious amounts of water. A syringe is fitted to the enteral tube, and water is forcibly instilled until patency is restored or the tube is abandoned. This method is frequently unsuccessful in clearing the tube, and generating high pressures in the enteral tube may cause the tube to rupture, potentially leading to dangerous patient aspiration. This means of unclogging tubes has been modified by using acidic solutions such as fruit juice and cola to try and dissolve pill fragments and the like; studies report variable success with this method.

Another approach to unclogging plugged enteral tubes is to use a proteolytic enzyme solution in an attempt to dissolve proteinaceous clogs. Examples include pancreatic enzymes and the commercially available Clog Zapper™. This method has utility against protein-based clogs, but may be unsuccessful for clogs caused by other materials, and the long duration required for the enzymatic solution to work ties up valuable nursing staff for extended periods of time.

A further, very successful means of unclogging an enteral feeding tube is to use a probe or wire inserted into the bore of the tube to mechanically dislodge the clog. The Bionix Development Corporation DeClogger™ is one such example; a plastic member with a screw thread molded into its distal tip is inserted into the enteral tube and worked through the clog using a twisting motion. While effective, the limited length of the plastic member limits the DeClogger's utility to tubes of shorter length.

The TubeClear from CorPak Medsystems is another device that mechanically dislodges clogs. A TubeClear stent is introduced into the enteral tube and fed down the tube until it reaches the clog. The TubeClear is then attached to a base unit. A reciprocating motor in the base unit causes a wire member inside the stent to move forward and rearward at high speed; with each cycle the wire member extends past the stent sheath a short distance, impacting the clog. The rapid reciprocal action of the wire member against the clog causes it to break up and dislodge, restoring tube patency. While effective, the TubeClear is expensive to use and requires skilled nursing staff to administer and monitor the process.

SUMMARY OF THE INVENTION

In accordance with a preferred embodiment of the invention, a device is provided for unclogging a clogged enteral tube. The device includes a first length of tubing with a proximal end and a distal end, the first length of tubing defining a fluid channel, the distal end of the first length of tubing being fitted with a connector for connecting to an enteral feeding tube, and the proximal end of the first length of tubing being fitted with a connector that is not compatible with an enteral feeding tube. An anti-reflux valve is situated distal to the proximal end of the first length of tubing, the anti-reflux valve allowing fluid flow only towards the distal end of the first length of tubing. A second length of tubing is provided that has a proximal end and a distal end, the proximal end of the second length of tubing being connected to and in fluid communication with the first length of tubing at a position between the proximal end of the first length of tubing and the directional valve. A pressure relief valve is situated in-line between the proximal and the distal ends of the second length of tubing.

In another aspect of the invention, a method is provided for unclogging a clogged enteral tube. In accordance with the method, the device of the invention is connected to a water delivery device capable of providing a source of water under pressure to the connector at the proximal end of the first length of tubing. The connector at the distal end of the first length of tubing device is connected to a mating connector at the proximal end of the clogged enteral tube. Then, a water flow is initiated by means of actuating the water delivery device, providing a flow of pressurized water directed into the clogged enteral feeding tube until the clog has been dislodged or fragmented and the enteral tube is restored to patency. In a preferred embodiment, the water flows in a pulsatile flow pattern.

BRIEF DESCRIPTION OF THE DRAWINGS

The advantages of the invention will become readily apparent to those skilled in the art from the following detailed description of various embodiments when considered in the light of the accompanying drawings, in which.

DETAILED DESCRIPTION OF THE INVENTION

Figure 1:
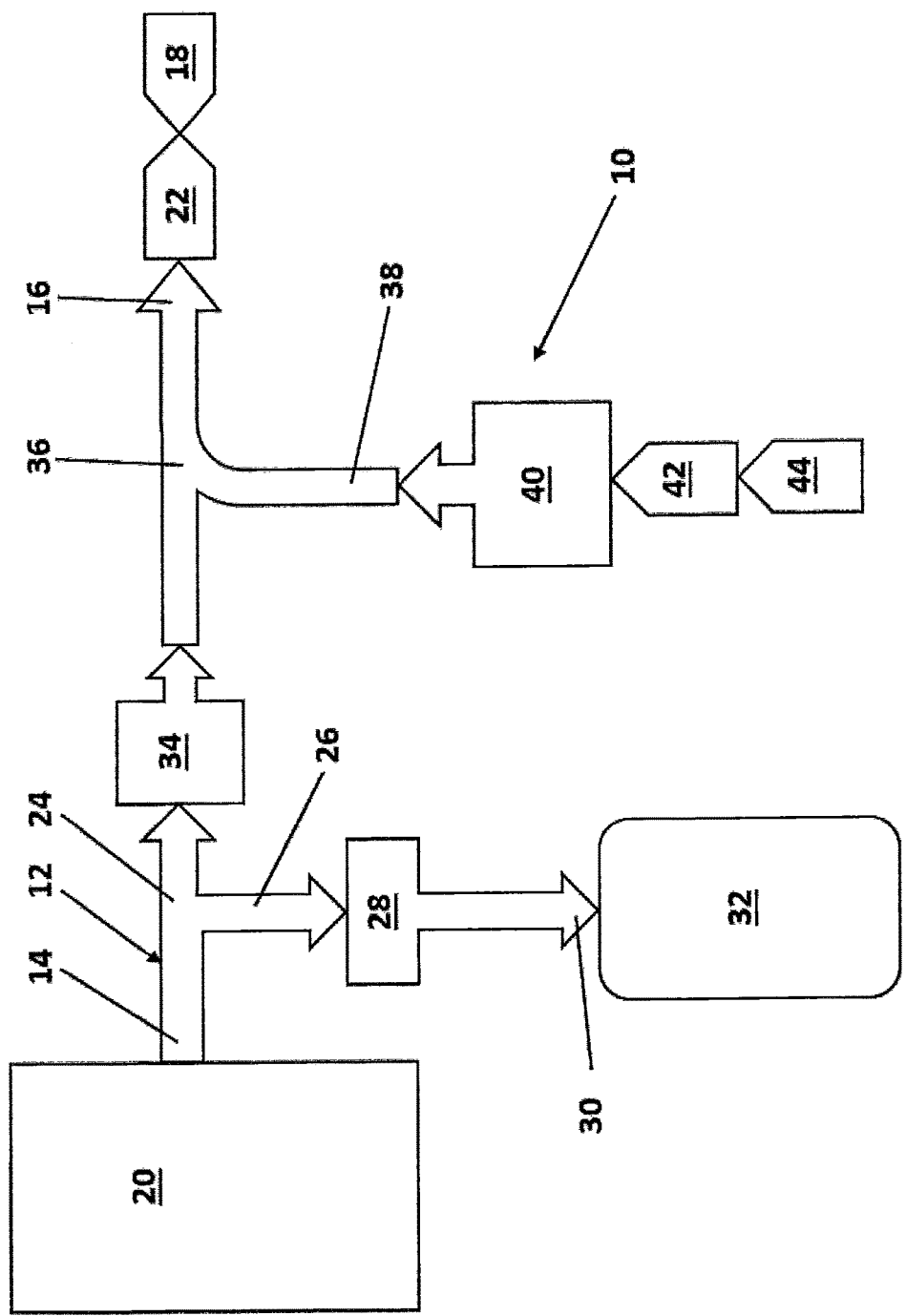
FIG. 1 is a schematic view of a medical tube unclogging system in accordance with a preferred embodiment of the invention.

The current invention presents a novel and safe mechanical approach to clearing a clogged enteral feeding tube that avoids the risks and complications of the above procedures and devices. The current invention uses a stream of water, preferably a pulsatile stream of water, to gently dislodge and flush clogs from the tube. Elements of the invention prevent siphoning of potentially biohazardous material back to the water source, and provide protection from the build-up of over-pressures that could rupture the tube.

The current invention includes a first length of tubing or main tube with a proximal end and a distal end. Of course, a "length of tubing" is used herein to mean a single piece of tubing or multiple pieces of tubing interconnected in a linear fashion. The distal end of the main tube is preferably fitted with an ENFit connector. ENFit is the new enteral feeding tube connector that was recently adopted pursuant to International Standards Organization, ISO 80369-3, and has been designed to reduce the risk of misconnection of enteral nutrition systems with other types of connectors, such as Luer fittings on IV's. The ENFit connector at the distal end of the invention will allow it to connect readily and securely to feeding tubes of all types and sizes.

The proximal end of the main tube of the invention will be fitted with a different tubing connector that will by design and intent NOT be compatible with the connector on the distal end of the main tube; that is, the ENFit system connector. In the preferred embodiment of the invention, this connector includes a direct connection to the water delivery unit. Using a unique connector of this sort will ensure that no misconnection of the proximal end of the main tube to the enteral feeding tube can occur.

Distal to the proximal end of the invention will be an in-line anti-reflux valve. Such valves can take several forms, a simple example being a duck-bill valve with directional flow. The placement of such a directional valve in this location will prevent siphoning or reflux of potentially bio-hazardous material retrograde into the water source.

Proximal to the anti-reflux valve, but distal to the direct connection to the water delivery unit, will preferably be situated a 3-armed "tee"; the proximal arm of the "tee" connects to the proximal portion of the tube distal to the direct connection to the water delivery unit. The distal arm of the "tee" connects to the distal portion of the tube but proximal to the anti-reflux valve. The middle arm of the "tee" connects to a pressure relief valve. The pressure relief valve is designed so that it has a "cracking" pressure of less than the burst pressure of the enteral tube itself. In practice, a safety margin will be used to ensure that the pressure relief valve will open well before the pressure inside the enteral feeding tube reaches burst pressures. A short length of tubing and collection reservoir may be optionally connected to the outlet of the pressure relief valve to allow for the safe and sanitary capture of any overflow run-off solution.

In practice, the invention will be first connected via the direct connection to the water delivery device at its proximal end to an electro-mechanical pumping device providing a source of pressurized water. The water may be provided in a pulsatile flow pattern or a steady state flow pattern, but preferably the flow is pulsatile. An example of such an electro-mechanical pumping device would be a dental irrigator. The distal end of the invention is then connected via the female ENFit connector to the mating male ENFit connector on the enteral tube. The pump is filled with water, and the device turned on. Water quickly fills the enteral tube. The pressure relief valve prevents tube rupture by "cracking" open to relieve excess pressure and redirect water as needed. Because water is incompressible, the pulsating pressure wave works against the clog until it softens and breaks up or dislodges, restoring patency to the enteral tube. The invention is then disconnected from the enteral tube ENFit connector, and enteral tube patency is demonstrated by the instillation of a small amount of water or other liquid. The invention is then disconnected from the pump source and discarded. The invention is intended to be a single patient use device.

Figure 2:
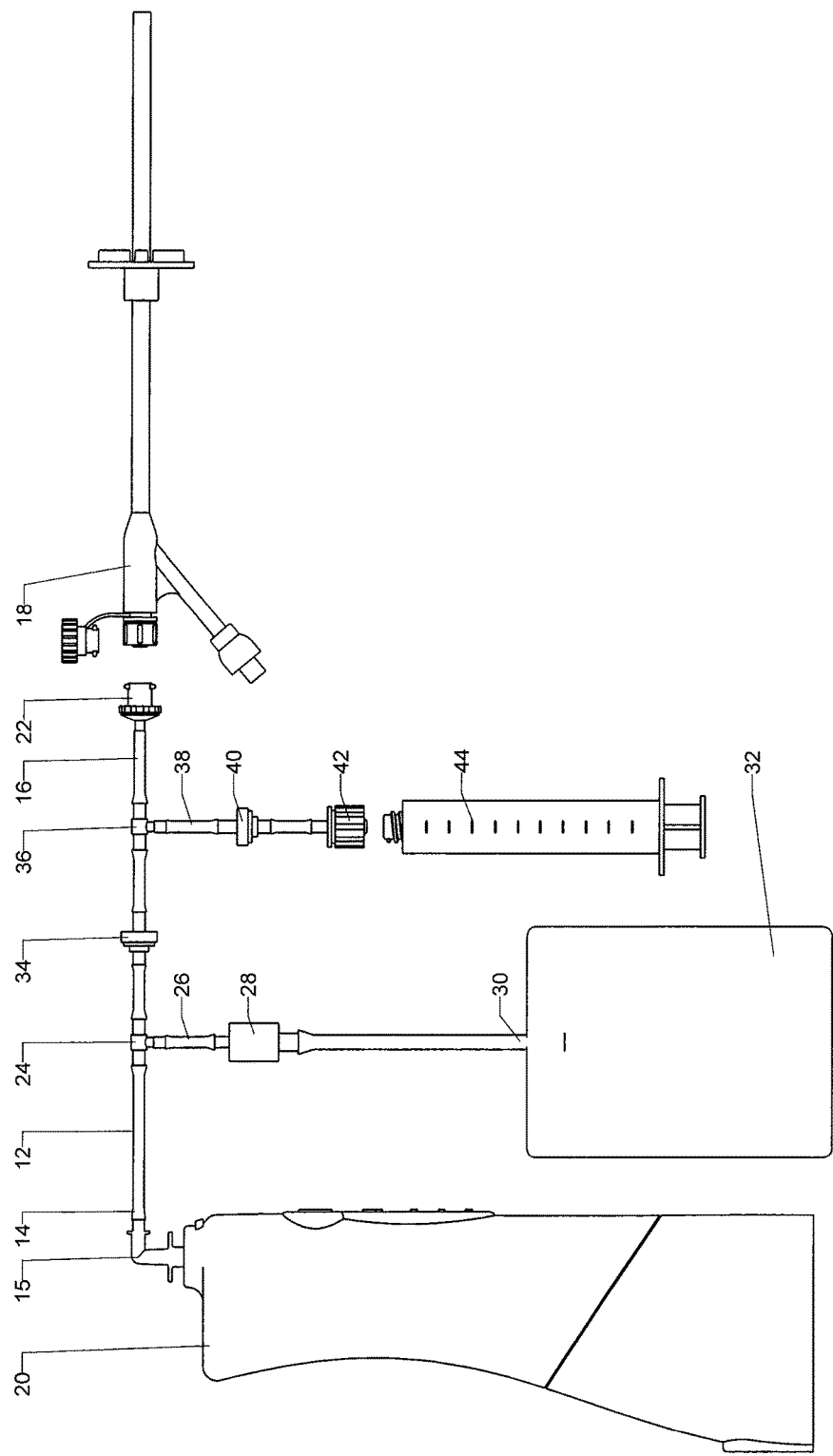
FIG. 2 is a plan view of the medical tube unclogging system of FIG. 1.

Referring now to the drawings, FIGS. 1 and 2 illustrate a medical tube unclogging system 10 in accordance with a preferred embodiment of the invention. Shown in FIG. 1 is a first length of tubing or main tube 12 having a continuous and uninterrupted fluid pathway, with the arrows showing direction of fluid flow. The tube 12 is shown to have a proximal end 14 which functions as the fluid inlet to the tube 12, and a distal end 16 which functions as the fluid outflow from the main tube 12 to a feeding or enteral tube 18. The proximal end 14 of the tube 12 is shown to have a connector 15 allowing the direct connection of the main tube 12 to a water delivery unit 20 capable of providing a pulsatile flow of pressurized water. The distal end 16 of the tube 12 is shown to have connector of a type that is not compatible with the connector on the proximal end 14, preferably a female ENFit connector 22 (ISO 80369-3 compliant), that allows the unclogging device 10 to be unambiguously connected to a clogged enteral tube 18 only at the distal end 16 of the main tube 12 of the device 10.

Spaced distally from the direct connection to the water delivery unit 20 is positioned a "tee" juncture or proximal tee 24 where the tube branches, both tube segments distal to the proximal tee 24 having a continuous fluid path with that portion of the tube 12 extending from the water delivery unit 20. One branch tube segment forms the distal portion of the main tube 12 of the unclogging device 10. The distal end of this segment is connected to the female ENFit connector 22 as described above. The other distal branch tube segment defines a second length of tubing or overflow tube 26 in which is positioned an in-line pressure relief valve 28. In a preferred embodiment of the invention, this valve 28 is a ball check valve having an opening pressure that is less than the defined bursting pressure of the clogged enteral tube 18. It is recognized by those practiced in the art that other valve types may also be used to perform this function. Having the opening pressure of this in-line pressure relief valve 28 be less than the bursting pressure of the clogged enteral tube 18 prevents unexpected and potentially catastrophic rupture of the clogged enteral tube, and adds a significant safety factor to the use of the unclogging device 10. In a preferred embodiment of the invention, the outlet of this overflow tube 26 leads to an overflow reservoir, such as the bag 32, to contain overflow fluid. It is recognized by those skilled in the art that this tube 26 could also lead to a basin or other open container without compromising the intent or function of the unclogging device 10.

As noted, the main tube 12 branch off the proximal tee 24 leads to a female ENFit connector 22 that can be selectively connected to the clogged enteral feeding tube 18. Between the proximal tee 24 and the female ENFit connector 22 there is positioned in the main tube 12 an anti-reflux valve 34. This one-way valve performs an important function by acting as an anti-siphon valve to prevent backflow from contaminating the water delivery unit 20. The anti-reflux valve 34 also provides for an unambiguous directional water flow through the main tube 12. In a preferred embodiment of the invention, the valve 34 is an umbrella valve type; however, it is recognized by those practiced in the art that other valve types may also be used to perform this function.

Distal to the anti-reflux valve 34 is another "tee" connector, the distal tee 36, with a branch to a typically short third length of tubing or patency check tube 38. The patency check tube 38 is provided with a directional check valve 40 and ends with a connector that is preferably compatible with connector 22 on the distal end 16 of the main tube 12; that is, preferably a male ENFit style connector 42. This male ENFit connector 42 is intended to connect to an ENFit syringe 44, allowing the operator to check for patency after one or more unclogging attempts without disconnecting the female ENFit connector 22 from feeding tube 18. The additional directional or anti-reflux valve 40 ensures that fluid from water delivery unit 20 flows only into the enteral feeding tube 18, and that no fluid escapes through the distal end of the patency check tube 38.

It is recognized that the lengths of the tubing segments of the unclogging device as described above may be variable and adjusted in the preferred embodiment to provide for ease of use of the device in the clinical setting without detracting from the design and/or intended use of the device.

Figure 3:
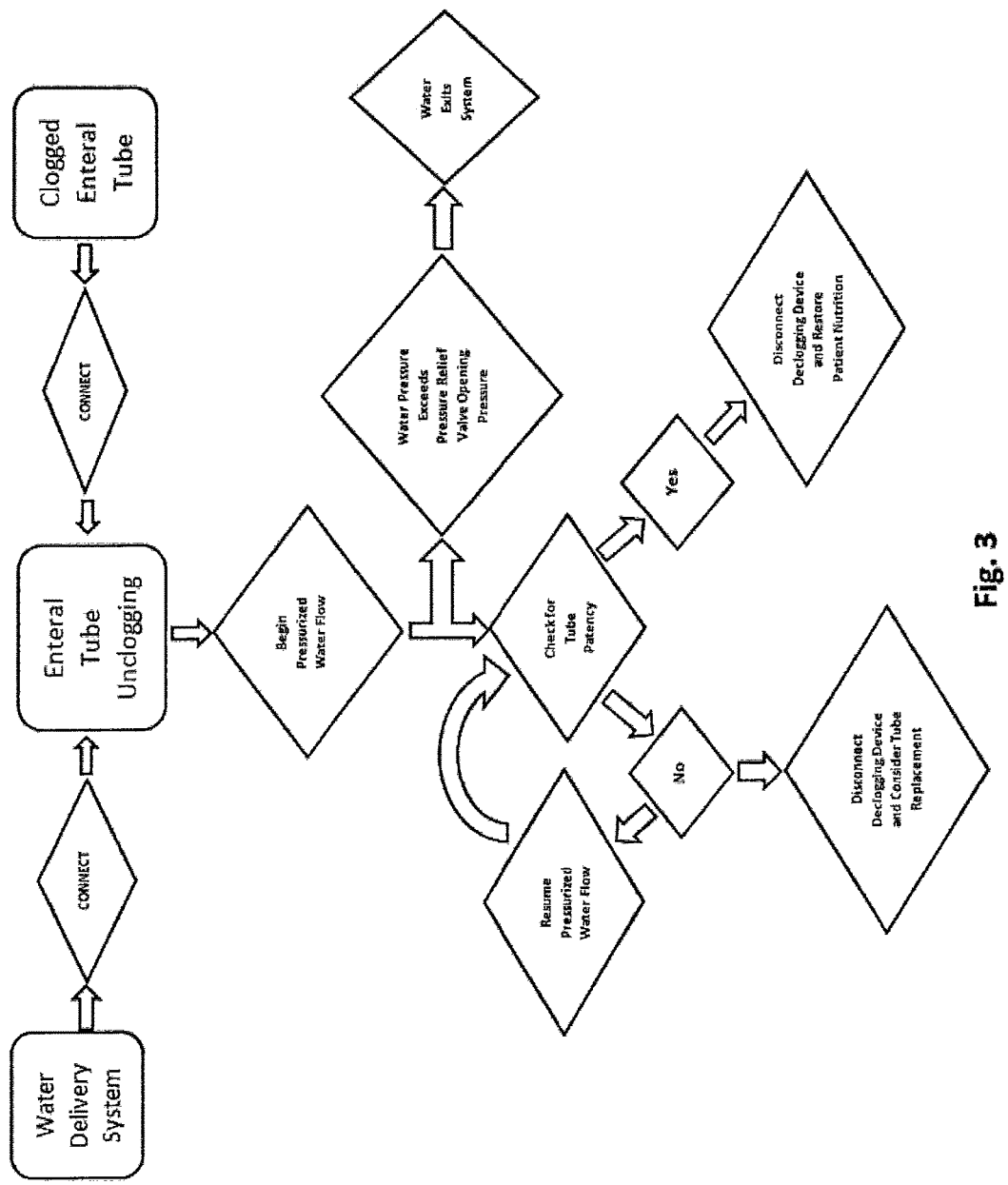
FIG. 3 shows a flowchart illustrating a method in accordance with a further aspect of the invention.

The flowchart of FIG. 3 illustrates a method in accordance with a further aspect of the invention. The flowchart shows the steps of first connecting the unclogging device of this patent to the source of pulsatile pressurized water and to the clogged enteral tube. The female ENFit connector at the distal end of the unclogging device ensures unambiguous connection only to the clogged enteral tube, while the direct connection to the water delivery unit at the proximal end of the device ensures unambiguous connection only to the source of pulsatile pressurized water. Because the connectors at the proximal end and distal ends of the unclogging device are dissimilar and specific to their mates, it is impossible to connect the unclogging device to either the water source or the enteral tube in any but the correct fashion and fluid flow direction.

In a preferred embodiment of the device, the source of pulsatile pressurized water is an electromechanical pump. It is recognized by those practiced in the art that other sources of pulsatile pressurized water may serve adequately in this capacity.

Following connection of the unclogging device to the water source and clogged enteral tube, the water source is engaged, and a pulsatile flow of pressurized water flows through the unclogging device into the clogged enteral tube. If the water pressure in the system exceeds the opening pressure of the pressure relief valve, the valve opens and water exits the system as shown; once the water pressure drops to safe levels the pressure relief valve closes and the flow of water exiting the system stops.

Preferably, after each unclogging attempt, the process is stopped and the enteral tube is tested for patency. If patency has been restored, the unclogging device and water supply are disconnected, and the patient is reconnected to his/her source of enteral nutrition or other. If patency has not been restored, the user has the option of resuming the process or declaring the tube unsalvageable and begin the separate process of replacing the enteral tube.

In accordance with the provisions of the patent statutes, the invention has been described in what is considered to represent its preferred embodiments. However, it should be noted that the invention could be practiced otherwise than as specifically illustrated and described without departing from its spirit or scope.

What is claimed is:

1. A method for unclogging a clogged enteral tube, comprising:
   providing a device for unclogging a clogged enteral tube comprising:
      a first length of tubing with a proximal end and a distal end, the first length of tubing defining a fluid channel, the distal end of the first length of tubing being fitted with a first connector for connecting to an enteral feeding tube, and the proximal end of the first length of tubing being fitted with a second connector that is not compatible with an enteral feeding tube;
      an anti-reflux valve situated distal to the proximal end of the first length of tubing, the anti-reflux valve allowing fluid flow only towards the distal end of the first length of tubing;
      a second length of tubing having a proximal end and a distal end, the proximal end of the second length of tubing being connected to and in fluid communication with the first length of tubing at a position between the proximal end of the first length of tubing and the anti-reflux valve; and
      a pressure relief valve situated in-line between the proximal and the distal ends of the second length of tubing;
   connecting a water delivery device for providing a source of water under pressure to the second connector at the proximal end of the first length of tubing;
   connecting the first connector at the distal end of the first length of tubing device to a mating connector at the proximal end of the clogged enteral tube; and
   unclogging a clogged enteral tube by actuating the water delivery device, to provide a flow of pressurized water into the clogged enteral feeding tube until the clog has been dislodged or fragmented and the enteral tube is restored to patency.

2. The method of claim 1, the device for unclogging a clogged enteral tube further comprising a third length of tubing having a proximal end and a distal end, the proximal end of the third length of tubing being connected to and in fluid communication with the first length of tubing at a position between the distal end of the first length of tubing and the anti-reflux valve, and the distal end of the third length of tubing having a third connector for connecting to an enteral feeding syringe.

3. The method of claim 1, the device for unclogging a clogged enteral tube further comprising an overflow reservoir connected to the distal end of the second length of tubing.

4. The method of claim 1, wherein the second connector on the proximal end of the first length of tubing is a Luer style connector.

5. The method of claim 1, wherein the second connector on the proximal end of the first length of tubing is directly connected to the water delivery device.

6. The method of claim 1, wherein the first connector on the distal end of the first length of tubing is an ISO 80369-3 compliant connector and the second connector on the proximal end of the first length of tubing is incompatible with an ISO 80369-3 compliant connector.

7. The method of claim 1, wherein the anti-reflux valve comprises a duckbill valve.

8. The method of claim 1, wherein the anti-reflux valve comprises a ball/spring valve.

9. The method of claim 1, wherein the anti-reflux valve comprises a dome valve.

10. The method of claim 1, wherein the pressure relief valve comprises a head-pressure valve.

11. The method of claim 1, wherein the pressure relief valve comprises a duckbill valve.

12. The method of claim 1, wherein the pressure relief valve comprises a ball/spring valve.

13. The method of claim 1, wherein the water delivery device comprises a motorized pump and a water reservoir to selectively provide a pulsatile flow of said pressurized water.

14. The method of claim 1, wherein the water delivery device comprises a hand actuated pump and a water reservoir to selectively provide a pulsatile flow of said pressurized water.

15. The method of claim 1, wherein the water delivery device comprises a hand actuated syringe with a spring-return plunger to provide a pulsatile flow of pressurized water.

16. The method of claim 1, wherein the water delivery device comprises a hand actuated syringe, wherein the syringe having a plunger is filled only partially with water and partially with air, the air inside the syringe comprising a compressible medium such that by repeatedly depressing the plunger and then releasing the plunger a pulsatile pressure wave is generated within the water inside the syringe.

17. The method of claim 2, wherein the third connector on the distal end of the third length of tubing is an ISO 80369-3 compliant connector.

* * * * *